(12) United States Patent
Knobel

(10) Patent No.: US 8,239,137 B2
(45) Date of Patent: Aug. 7, 2012

(54) ANALYTICAL METHOD AND INSTRUMENT

(75) Inventor: Rolf Knobel, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1466 days.

(21) Appl. No.: 11/639,947

(22) Filed: Dec. 15, 2006

(65) Prior Publication Data

US 2007/0166744 A1 Jul. 19, 2007

(30) Foreign Application Priority Data

Dec. 19, 2005 (EP) .................................... 05112359

(51) Int. Cl.
*G01N 33/48* (2006.01)
*G06G 7/48* (2006.01)
(52) U.S. Cl. ........................................... 702/19; 703/11
(58) Field of Classification Search .................. None
See application file for complete search history.

(56) References Cited

U.S. PATENT DOCUMENTS 4,028,182 A * 6/1977 Zajic et al. ...................... 435/250
7,680,603 B2 * 3/2010 Kurnik ............................ 702/19

FOREIGN PATENT DOCUMENTS

| EP | 0686699 B1 | 12/2004 |
| EP | 1701275 A2 | 9/2006 |
| WO | WO 97/46714 A1 | 12/1997 |

OTHER PUBLICATIONS

Hau, B., et al., 1993, "Mathematical Functions to Describe Disease Progress Curves of Double Sigmoid Pattern", *Phytopathology*, 83:928-932.
Tichopad, Ales, et al., 2002, "Improving quantitative real-time RT-PCR reproducibility by boosting primer-linked amplification efficiency", *Biotechnology Letters*, 24:2053-2056.
Liu, W., et al., 2002, "Validation of a Quantitative Method for Real Time PCR Kinetics", *Biochemical and Biophysical Research Communications*, 294: 347-353.
Zhao, S., et al., 2005, "Comprehensive Algorithm for Quantitative Real-Time Polymerase Chain Reaction", *Journal of Computational Biology*, 12 (8):1047-1064.

* cited by examiner

*Primary Examiner* — Eric S Dejong
(74) *Attorney, Agent, or Firm* — M. Reza Savari; Charles M. Doyle

(57) ABSTRACT

Subjects of the invention are a method for determination of an analyte using a particular algorithm based on a mathematical model for transforming measurement data into a growth curve and an analytical instrument comprising a computing unit for more precise determination of an analyte.

8 Claims, 3 Drawing Sheets

ANALYTICAL METHOD AND INSTRUMENT

This application claims the benefit of priority under 35 U.S.C. §119 of EP Application 05112359.4, filed Dec. 19, 2005, the contents of which are hereby incorporated by reference.

BACKGROUND OF THE INVENTION

1. Field of the Invention

The present invention provides a method for the determination of the presence of an analyte and an analytical instrument capable of performing the method.

2. Description of Related Art

The invention is useful in the field of analytics or diagnostics, particularly in the diagnostics of nucleic acids. The analysis of nucleic acids has been improved considerably by the invention of the Polymerase Chain Reaction (PCR) as disclosed in EP 0 200 362 and EP 0 201 184. During the course of this method, the amount of nucleic acids is increased at least partially exponentially, as theoretically from each nucleic sequence present in the reaction mixture in each reaction cycle an additional nucleic acid is created, and each of the nucleic acids can act as a template for the creation of a further nucleic acid sequence in the following reaction cycle. The amount of nucleic acids created is limited by e.g., the amount of reagents, like enzymes, primers and nucleotides, contained in the reaction mixture. Therefore, the concentration plotted versus the time or cycle number of the PCR resembles an (asymmetric) sigmoid curve.

A further improvement of PCR is the so-called Real-Time-PCR. In this method, a signal is created and detected during amplification. The signal is representative of the amount of nucleic acids created during amplification and thus present in the reaction mixture. In a first embodiment, e.g. disclosed in EP 0 512 334, the signal is created by a compound capable of intercalating into double stranded nucleic acids while changing its fluorescence properties. In another embodiment, as disclosed in EP 0 543 942, each extension reaction of a primer leads to the cleavage of a probe, labeled by a quencher and an emitter dye such that when cleaving the probe, the quencher cannot quench the light emission of the reporter dye, so that a signal can be detected.

The determination of the amount of nucleic acid originally present in the sample prior to amplification (quantification or quantitation) has been the goal of several investigations. Generally, the higher the amount the smaller the number of reaction cycles needed to receive a defined intensity of the signal (threshold). The earliest calculations therefore were based on the determination of the threshold cycle ($C_T$)-value. The higher the $C_T$-value, the lower the original amount of nucleic acid present. Obviously, the (integer) number of reaction cycles conducted can only be a very rough estimate of the amount originally present. Thus, in a further attempt to determine concentrations the signal intensities lying between distinct measurement data were interpolated (linear or logarithmically). These interpolation based methods have some deficiencies, e.g., they are sensitive to the presence of imprecise signal measurements or measurement outliers (e.g., spikes). To avoid this, algorithms have been established to create continuous growth curves from a defined number of measurements during the amplification reaction. One example of such an algorithm is the so-called Sawitzky Golay Filter. In EP 0 686 699 there is described a conditional recursive formula which can be used for fitting of measured data to a theoretical curve. However, the application is cumbersome and the fitting process is not described. The algorithm lead to strong parameter correlations and inaccurate results in certain cases.

In WO 97/46714 methods of monitoring hybridization after polymerase chain reaction (PCR) are disclosed. In particular, the application discloses that the sensitivity of an initial template quantification with fluorescence vs. cycle number plots can be increased by analysis of product melting curves to control for nonspecific amplification and by nonlinear regression fitting Levenberg-Marquard curve-fitting algorithms.

In Biotechnology Letters 24, 2002, 2053-2056 there is disclosed a method to determine the amplification efficiency of RT-PCR using a four parametric sigmoid model.

In Biochemical and Biophysical Research Communications 294, 2002, 347-353 there is also described a PCR simulation method for determining the efficiency of PCR.

These two mathematically equivalent four parameter models provide limited accuracy especially in the areas which usually are critical for an exact result calculation. The baseline is forced to be constant and the simple sigmoid term is not capable of approximating the full complexity of a general growth curve. Therefore, the exponential phase is approximated with limited accuracy as can be visually observed in the graphs of the two papers. This leads to a result with limited accuracy, e.g. $C_T$.

It was the object of the present invention to improve the quantitative analysis, particularly to provide a fully automatic method using a mathematical calculation to better estimate the whole growth curve, especially to correct measurement imprecision and possible measurement spikes.

SUMMARY OF THE INVENTION

In a first embodiment, the invention is directed to a method for determining the presence of a nucleic acid in a sample, comprising:

providing a reaction mixture containing said nucleic acid, detecting signals from said reaction mixture in known intervals, transforming said signals into measurement data, and creating from said measurement data a growth curve through a mathematical algorithm, wherein said mathematical algorithm comprises a mathematical growth curve model formula depending on between 5 and 11 parameters and wherein the optimal values of said parameters are determined by applying a regression fitting algorithm to said measurement data, said growth curve model formula at least comprising a background curve estimation, a saturation curve estimation, and an intermediate growth curve estimation according to the formula $$1/(1+\exp(-p_4(x-p_5)))/(1+\exp(-p_6(x-p_7)))$$

wherein $p_4$ is the slope at the inflection point of a first multiplicative sigmoid function representing exponential growth, $p_5$ is the inflection point of a first multiplicative sigmoid function, $p_6$ is the slope at the inflection point of a second multiplicative sigmoid function representing saturation growth, and $p_7$ is the inflection point of a second multiplicative sigmoid function.

Another subject of the invention is an analytical instrument for determining the presence of an analyte in a sample comprising a light source,
a signal detection unit,
a signal to measurement data transformation unit,
a measurement data storage,
a measurement data to growth curve transformation unit, and
a growth curve interpretation unit,
wherein said measurement data to growth curve transformation unit comprises a computer loaded with a fully automatic algorithm for non-linear regression fitting of a growth curve to the measurement data using a mathematical algorithm comprising a mathematical growth curve model formula depending on between 5 and 11 parameters, wherein the optimal values of said parameters are determined by applying a regression fitting algorithm to said measurement data and wherein said growth curve model formula at least comprises
a background curve estimation,
a saturation curve estimation, and
an intermediate growth curve estimation according to the formula $$1/(1+\exp(-p_4(x-p_5)))/(1+\exp(-p_6(x-p_7)))$$

wherein
$p_4$ is the slope at the inflection point of a first multiplicative sigmoid function representing exponential growth,
$p_5$ is the inflection point of a first multiplicative sigmoid function,
$p_6$ is the slope at the inflection point of a second multiplicative sigmoid function representing saturation growth, and
$p_7$ is the inflection point of a second multiplicative sigmoid function.

Another subject of the invention is a computer program for determining the presence of an analyte from measurement data comprising
creating a growth curve from measurement data through a mathematical algorithm,
wherein said mathematical algorithm comprises a mathematical growth curve model formula depending on between 5 and 11 parameters and wherein the optimal values of said parameters are determined by applying a regression fitting algorithm to said measurement data, said growth curve model formula at least comprising
a background curve estimation,
a saturation curve estimation, and
an intermediate growth curve estimation according to the formula $$1/(1+\exp(-p_4(x-p_5)))/(1+\exp(-p_6(x-p_7)))$$

wherein
$p_4$ is the slope at the inflection point of a first multiplicative sigmoid function representing exponential growth,
$p_5$ is the inflection point of a first multiplicative sigmoid function,
$p_6$ is the slope at the inflection point of a second multiplicative sigmoid function representing saturation growth, and
$p_7$ is the inflection point of a second multiplicative sigmoid function.

DETAILED DESCRIPTION OF THE INVENTION

Figure 1:
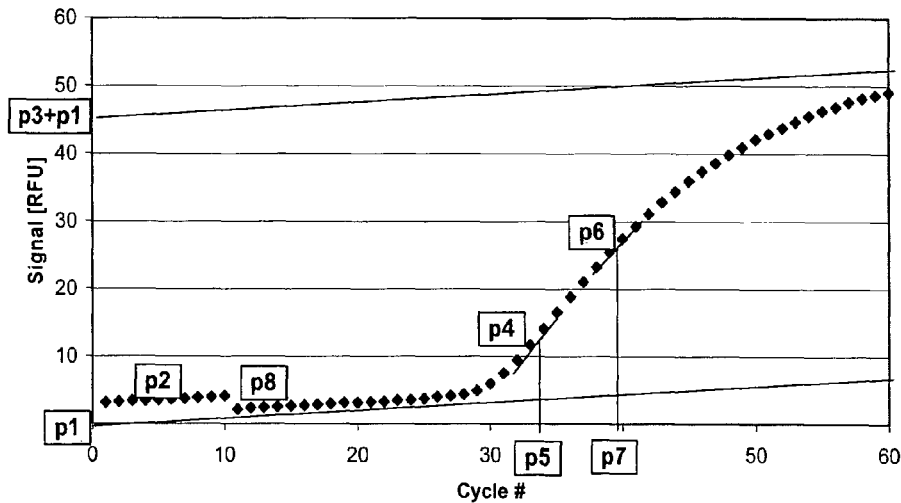
In FIG. 1 there is depicted a growth curve showing exemplary model parameters.

While the invention is useful for the determination on any analyte, in most of the following the invention is exemplified for the determination of nucleic acids. Methods for determining the presence of a nucleic acid in a sample are generally known. They usually are based on the detection of the occurrence of hybridization of nucleic acid probes, e.g. oligonucleotides, to the nucleic acid to be determined, i.e. the formation of hybrids. However, there are also methods using detecting the interaction of other chemical compounds with the nucleic acid to be determined or with compounds derived therefrom, e.g. detecting the occurrence of intercalation of intercalating dyes into double stranded nucleic acids. Regardless of the detection method chosen, the present invention provides means to determine the analyte by tracking the course of a reaction over a period of time, e.g. by collecting data received from said tracking and interpreting the data received. The present invention therefore is particularly useful for tracking of reactions in which a detectable change in the sample is a measure of the absence, presence or/and the amount of the analyte present in said sample. Those determinations are also called kinetic determinations.

As used herein, a "sample" is a liquid that may contain the analyte, e.g. the nucleic acid or/and any nucleic acids derived therefrom, e.g. any products of an amplification reaction, in which the presence of the nucleic acid is to be determined. The original sample may or may not contain the analyte in an original concentration or amount. The present invention is capable of determining whether the analyte is present at all. The present invention can also support and improve the determination of the amount or concentration of the analyte in the original sample. The pre-processing of the measurement data results in a continuous statistical imprecision-free growth curve. Quantification measures (e.g. $C_T$) derived there from have an improved robustness and accuracy compared to present methods.

A sample may also be a liquid derived from the original sample by removing or adding components. For example, it is widely recognized that the determination of nucleic acids in a sample is improved, if the nucleic acids are isolated or purified and thereafter are dissolved in a liquid allowing the determination to take place. Such nucleic acid purification is generally known to those skilled in the art. It is also well known to relate the amount of nucleic acids originally present in a sample with the amount of nucleic acids present in a sample derived from said original sample. Again, it is well known to determine the concentration of the nucleic acid in said original sample volume from the amount or concentration of nucleic acids present in the sample derived therefrom.

Original samples may be taken from any source. In health care, common samples are samples taken from the body, preferably the human body, such as blood or urine, or samples derived therefrom, like serum or plasma. In food analysis, samples may be direct liquids, such as juice, but may also be liquids derived from solid samples, like extracts from fruit, cheese or meat.

As mentioned above, many samples, particularly in the nucleic acid determination field, require isolation of the analyte from components in the sample disturbing the analysis. Such isolation is well known to the man skilled in the art.

The method according to the invention comprises adding to the sample the reactant and all compounds needed for the reaction to occur, thus creating a reaction mixture. This reaction mixture is the subject of the detection. The reaction mixture can be provided during the detection part of the method, but preferably is done prior to the start of the detection.

The present invention includes detecting a signal from the reaction mixture. This signal should be related with the reaction occurring, if any, in the reaction mixture. Therefore, any reaction during which a signal can be created that can be detected can be monitored in the process according to the present invention. The signal can be any signal that is detectable, e.g. electrochemically or electromagnetically. In some embodiments, the signal is an electromagnetic signal, e.g., an electromagnetic wave of a particular characteristic, such as light, be it visible or invisible to the human eye. Instruments or devices for detecting such signals are generally known in the art. Such a signal may be a chemiluminescent, fluorescent, or radioactive signal.

In certain embodiments, the method for the determination of nucleic acids includes amplification of nucleic acid sequences to be detected. One of the methods for amplification of nucleic acids is the polymerase chain reaction (PCR, disclosed in EP 0 201 184 and EP 200 362). This method is a process comprising the steps of subjecting double stranded nucleic acids in a reaction mixture to reversibly denaturing conditions, e.g. by heating above the melting temperature of the double stranded nucleic acids; annealing a primer to each of the single stranded nucleic acids prepared; extending the primers by attaching mononucleotides to the ends of said primers using the sequence of the single stranded nucleic acid as a template for newly formed sequences; and repeating the above steps a desired number of times. This reaction cycle is repeated as many times as desired, using extension products of the earlier cycles as templates for the extension of primers in the next cycles, to prepare as many extension products as needed to allow their detection. It has proven convenient to repeat the reaction cycle between 10 and 100 times, or between 20 and 60 times. The amount of cycles needed for detectable nucleic acid creation may depend upon the amount of a nucleic acid to be determined. For example, for analyte nucleic acids usually present in the sample in very tiny amounts, as in the case of an infection with Human Immunodeficiency Virus (HIV) or Hepatitis C Virus (HCV), conducting the analysis will be expected to take more cycles than for analytes usually present in higher concentrations. These considerations are known to those skilled in the art.

In certain embodiments, the amplification of the nucleic acids in the reaction mixture is the reaction monitored. In this case, any increase of the amount of nucleic acids, particularly those representative for the presence or/and the amount of the analyte nucleic acid, is determined using a signal detected during the course of the reaction. Those methods based on PCR are usually referred to kinetic PCR methods, or real time PCR methods. Examples of such reactions are those disclosed in EP 0 512 334, EP 0 543 942 and WO 97/46714.

The signal may be a signal that is created during the course of the reaction without any further action, i.e. a rise in temperature of the reaction mixture caused by the energy set free by the reaction. In certain embodiments, the sample is subjected to an influence from outside, e.g. by providing energy to the reaction mixture. This energy usually is provided in a form suitable for eliciting a detectable signal from the reaction mixture, e.g. a label contained in the mixture, which is correlated with the course of the reaction occurring in the reaction mixture. In one embodiment, the energy is provided by applying light irradiation to the reaction mixture. The light should have the property to provoke a signal from the reaction mixture related to the reaction occurring.

In certain embodiments, the detectable signal is in the form of light escaping from the reaction mixture. In case of irradiating the reaction mixture with light, this light may have the same characteristic as the light used for irradiation. Then the detection is absorption detection. In other embodiments, the light escaping the reaction mixture is different from the irradiating light. In this case, the escaping light preferably is created by a fluorescence process. The fluorescent light will be detected as a measure of the course of the reaction.

This signal is detected in known intervals. An interval is the time between subsequent detections, preferably not counting duplicates. Those intervals are chosen to adequately monitor the course of a reaction or a number of reactions performed in said sample. Therefore, the signals may be detected during the course of the reaction. While the detection may be started together with the start of the reaction, this is not required. The detection may be stopped when the reaction has come to completion, but may be stopped earlier or may be continued for some time after completion of the reaction. A person skilled in the art will know that when there are no significant changes of the signal any more, the detection can be stopped.

The intervals at which the signals are detected will depend upon the desired accuracy of the determination. Generally, the shorter the intervals are, the higher will be the accuracy. For kinetic PCR, preferably the length of each interval used for detection of the signal coincides with the time of one reaction cycle. If the lengths of the reaction cycles are identical, the intervals will be identical, too. It will be appreciated that each detection may be constituted by a series of measurements within a very short time (e.g. below 1% of, the interval as mentioned above). Preferably, in PCR, a signal is detected more than once, or between 2 and 10 times, during a plateau phase of each cycle. A plateau phase in a particular PCR cycle is a phase wherein the temperature of the reaction mixture is not substantially changed over time. Usually, this is the annealing phase of each cycle. This may be used to exclude instrument mistakes. For PCR, the length of one interval may be between 0.1 sec and 1 hr, or between 1 sec and 10 min, or between 5 sec and 1 min.

In other nucleic acid amplification/detection methods, like NASBA (nucleic acid sequence-based amplification) or SDA (strand displacement amplification), the cycles may not be clearly separated from each other by distinct process steps. Therefore, the intervals for detecting the signal can be chose more deliberately. For example, the intervals during such reactions may be between 0.1 sec up to 2 min, or between 1 sec and 1 min, or between 2 sec and 20 sec.

The signal may be created during the reaction as a result of the reaction without further inducement. The signal may be induced by providing energy to the reaction mixture, such as electrochemical or electromagnetic energy. The method according to the invention may include irradiating the reaction mixture with electromagnetic waves, e.g., with light. The light may be chosen such that it interacts with components in the reaction mixture dependent from the progress of the reaction to be monitored. In these embodiments, any components of the reaction or components related with components of the reaction are designed to absorb the light irradiated to the reaction mixture. Therefore, such methods are based on irradiating the sample with light having a particular characteristic and detecting light escaping said sample.

The characteristics of the light chosen to be impinged on said sample will depend upon the particular format and components of the sample. Assay formats well known to those skilled in the art make use of light absorbing labels, e.g. label attached to an oligonucleotide probe designed to hybridize to the nucleic acid to be determined, or a light absorbing chemical compound. Those formats include the change of a detectable property, e.g. a property caused by the change of the composition of the sample over time, e.g., the absorption or emission of light. This change of the property caused by said reaction is determined by detecting a signal received from said sample during the time of the reaction. In hybridization based formats a signal related to one or more labels attached to one or more oligonucleotide probes hybridizing to a target nucleic acid, or with nucleic acids derived therefrom, is detected.

Reactions that can be measured using the methods of the present invention are disclosed in EP 0 512 334 and EP 0 543 942, the disclosure of which is incorporated herein in their entirety regarding the conditions to run those reactions.

When required, each signal is transformed into measurement data. In certain embodiments, this is in the form of a digital number that can be stored electronically in a storage medium, such as a hard drive, CD, DVD, flash memory and the like. Suitable storage media are well known as memory in computer business, e.g. in personal computers. The transformation can be done according to methods widely known in the art, e.g. analog/digital converters. From said storage, the measurement data can be read to be subject of calculations using those data. During this process, the data may be subject to further manipulations, e.g. dark signal correction and multi-channel resolution. The result of this will be called measurement data.

In the next step, the measurement data are transformed into the continuous growth curve. A core aspect of the present invention is that this transformation is done by using a mathematical non-linear growth curve model formula using between 5 and 11 parameters and an algorithm for non-linear regression fitting of the growth curve to the measurement data. A non-linear formula is a formula which is not based on a linear relation of the parameters. Non-linear regression is described in general terms in: D. M. Bates, D. G. Watts: Nonlinear Regression Analysis and its Applications, Wiley (1988).

A growth curve model is a mathematical formula that describes the continuous dependence of a signal function from a time variable. The signal value is defined as a measure of the detected signal. The time variable is defined as integer cycle number when the signal is measured and its continuous extension. Preferably, this model contains between 7 and 10, or 9 parameters, including the signal value and the time variable. This number of parameters has been found to be accurately approximate the real growth curve, but does not overparameter it (i.e., high correlation between parameter).

In some embodiments, one more more of the parameters may be selected from the group consisting of measurement data (signal), time (cycle number), baseline intercept, relative drift, growth, slope 1, inflection 1, slope 2, inflection 2 and another parameter describing a curve characteristic. In some embodiments, the parameters are measurement data (signal), time (cycle number), baseline intercept, relative drift, growth, slope 1, inflection 1, slope 2, and inflection 2. Details and definitions can be taken from Table 1.

TABLE 1

| Parameter | Dimension | Name | Description |
|---|---|---|---|
| F | Y | Measurement data, (Fluorescence signal) | relative fluorescence units |

TABLE 1-continued

| Parameter | Dimension | Name | Description |
|---|---|---|---|
| X | X | Time, Cycle number | data points, integers |
| p1 | Y | Baseline Intercept | unquenched signal part |
| p2 | 1/X | Relative drift | slope of linear negative signal |
| p3 | ΔY | Saturated growth above negative signal | fluorescence increase |
| p4 | 1/X | Slope 1 | <ln(2) |
| p5 | X | Inflection 1 | Exponential phase |
| p6 | 1/X | Slope 2 | >0 |
| p7 | X | Inflection 2 | Middle of Growth |
| p8 | Y | (optional) step parameter | Step Size |

While the signal value (input from measurement) and the time variable are available from the measurement data, the other parameters are determined by applying a non-linear regression algorithm. Parameter $p_1$ represents the intercept of the growth curve with the y axis after an optional step (see $p_8$). The additional term $p_3/(1+\exp(p_4 \, p_5))/(1+\exp(p_6 \, p_7))$ is negligible in this definition. Parameter $p_2$ represents the relative drift of the negative baseline per cycle. Parameter $p_3$ represents the estimation of maximal growth of the value over the baseline. Parameter $p_4$ represents the slope of an approximate sigmoid function in the early exponential phase. $\exp(p_4)$ is an estimation of the amplification efficiency in that phase which means that $p_4$ is typically smaller than $\ln(2)$ for PCR. The related parameter $p_5$ represents the inflection point of that partial sigmoid function. The parameter $p_6$ represents the slope of an approximate sigmoid function in the saturation phase. The related parameter $p_7$ represents the inflection point of that partial sigmoid function. Parameter $p_7$ is higher than $p_5$ and $p_6$ and is smaller than $p_4$ in this definition. Optional parameter $p_8$ is the estimation of a signal step size occurring at a pre-set point because of a permanent change in measurement condition, usually a temperature change.

In some embodiments, the growth curve model in the algorithm has the following formula I.

$$f(x) = p_1 \cdot (1 + p_2 \cdot x) + \frac{p_3}{[1 + \exp\{-p_4 \cdot (x - p_5)\}] \cdot [1 + \exp\{-p_6 \cdot (x - p_7)\}]}$$

The definition of the parameters can be seen from Table 1.

In case of the measurement conditions, e.g., temperature, change at one point the model may have the mathematical representation of formula II comprising an additional term compared to the above formula I:

$$f(x) = p_1 \cdot (1 + p_2 \cdot x) + \frac{p_3}{[1 + \exp\{-p_4 \cdot (x - p_5)\}] \cdot [1 + \exp\{-p_6 \cdot (x - p_7)\}]} - \frac{p_8}{2} \cdot [1 + \text{sign}\{s - x + 0.5\}]$$

In this formula II, the additional variables are defined as follows:

sign: Signum function sign $(x) := x/\sqrt{(x^2)}, x < > 0$; sign $(0) := 0$.

s: pre-set step cycle number (cycle number at which a measurement condition, e.g. temperature has changed)

It is obvious to a person skilled in the art that the above formula can be written in different forms leading to the same result f(x). Those formulae are as well suitable as the model and are considered to be covered by the definition of the invention. Those rewritten formulae are called mathematical equivalents. A statistically sensible procedure is the transformation of the y measurement data to increase the y variance stability. Another transformation might reduce so called curvature effects in the non-linear regression algorithm. The proposed formulation is appropriate for constant measurement data variance over the whole range.

Figure 2:
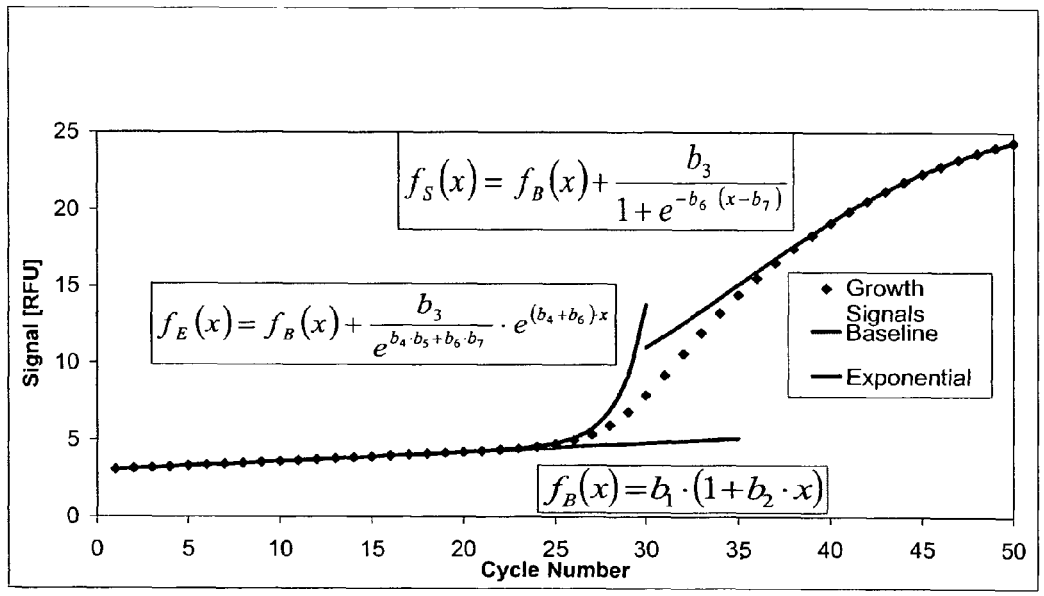
In FIG. 2 there is shown the growth curve with the exponential phase curve, the partial saturation sigmoid curve and the base line contributing to the growth curve model.

The interpretation of the model parameters can also be described with the help of the terms baseline, exponential phase and plateau (saturation) phase (See FIG. 2). The baseline starting phase $f_B$ is described with the linear formula $$vf_B(x)=p_1(1+p_2x)$$

The saturation or plateau phase $f_S$ is described with the sigmoid formula $$f_S(x)=f_B(x)+p_3/(1+\exp(-p_6(x-p_7)))$$

and the exponential phase is described with the exponential formula $$f_E(x) = f_B(x) + \frac{p_3}{e^{p_4 \cdot p_5 + p_6 \cdot p_7}} \cdot e^{(p_4+p_6)x}$$

For PCR the sum of $p_4$ and $p_6$ equals about $\ln(2)$ which refers to signal doubling after each cycle.

In one embodiment, the method according to the invention includes the step of determining an appropriate starting growth curve for the non-linear regression algorithm by automatically calculating from the measurement data an initial set of values for all parameters before starting a regression algorithm.

A sample initial set of values for the starting parameters is given in Table 2. Each of said parameters is either pre-set or can be calculated from the actual measurement data.

TABLE 2

| Parameter | Starting value description | Starting value formula |
|---|---|---|
| $p_1$ | Minimum | =Min (ydata) |
| $p_2$ | 0 | 0 |
| $p_3$ | Maximum − Minimum | =Max (ydata) − Min (ydata) |
| $p_4$ | 0.59 | =ln(1.8) |
| $p_5$ | X value after y reaching a quarter between p1 and p1 + p2 | =LOOKUP(Min(ydata) + 0.25 * (Max(ydata)−Min(ydata)); ydata;xdata)) |
| $p_6$ | 0.18 | =ln(1.2) |
| $p_7$ | X value after y reaching half between $p_1$ and $p_1$ + $p_2$ | =LOOKUP(Min(ydata) + 0.5 * (Max(ydata)−Min(ydata)); ydata;xdata)) |
| $p_8$ | 0 (optional step size parameter) | 0 |

The starting value estimation for parameter $p_1$ is the minimum of all measured data. For $p_2$ zero is used. The starting value estimation for parameter $p_3$ is the maximum of all measured data minus the minimum of all measured data. For parameter $p_4$ the starting value $\ln(1.8)=0.59$ is used. For the starting estimate of $p_5$ the number of the cycle is used in which the data has increased to 25% of the whole measurement data range.

For parameter $p_6$ the starting value $\ln(1.2)=0.18$ is used. For the starting estimate of $p_7$ the number of the cycle is used in which the data has increased the middle of the whole measurement data range.

The choice of the starting parameter values determines the amount of iterations needed and thus the length of the calculation procedure. The indicated choice of parameters and their values according to the present invention has surprisingly been found to considerably reduce this calculation effort.

Then, the resulting starting growth curve is iteratively adapted to the best fit, with the aim to produce a growth curve with parameters that best reflect the course of the reaction at any time, even between the times used for detecting the signal. In order to start the iterative adaptation of the growth curve, the parameters as used in the starting curve are altered. This can be done by known non-linear regression algorithms. Among those formulas are the nonlinear regression methods determining the minimal sum of deviations. Preferably this is done by minimizing the sum of square of deviations in y-direction. Preferably this done by a Levenberg-Marquardt or a Nelder-Mead simplex algorithm. The Levenberg-Marquardt algorithm uses a step-by-step increment process with simplified approximations for the second derivatives in the parameter. Furthermore, it is a combined optimization method which adapts automatically to the preferred (faster) one of its sub-methods. The Levenberg-Marquardt algorithm is generally known to those skilled in the art. In one embodiment of the present invention, a Levenberg-Marquardt algorithm is used in combination with the growth curve model according to the present invention. As stopping criterion for the algorithm it has been found that it is appropriate to stop after 5 iteration steps when each of the steps leads to less than a pre-set relative reduction of the sum of square deviation function. For this relative improvement limit $1\times10^{-2}$/number of cycle has been found to be appropriate for a reliable fully automatic calculation. If this is not reached within 100 iterations the algorithm is stopped anyway. It is appropriate to avoid numerical overflow to add a parameter limitation range (e.g. p3>0) for the following iteration to take place or penalty function to the optimization term (sum of square deviations).

The aim of the iteration is to find the optimum adaptation of the growth curve to the measurement data. During this process, a set of parameters is determined. The values for the optimized parameters of this set are called the optimized parameter values in the following. The growth curve containing the optimized parameter values is called the optimized growth curve. Preferably, the growth curve is a global growth curve. A global growth curve is a curve defined over the whole range of x values. It is evident that the denomination of the parameters ($p_1$ to $p_8$) is totally arbitrary. Other symbols can be chosen, e.g. a to h.

In case of almost linear curves there might be issues with overdetermination of the parameters possibly resulting in convergence to a local optimum of the sum of square deviations. In order to overcome this issue, one method is to use simplified models (e.g. $p_6=p_7=0$ or additionally $p_3=0.2$) and compare the regression results with the Schwarz Information Criterion (SIC) to select the model with the appropriate number of parameters.

Another application of the model is to use the standard error of y estimate to the model for a curve validity check. For scale invariance the following number is calculated and compared against a pre-set limit.

$$\frac{SEy}{Avg(y)} < \text{Relative Deviation Limit}$$

SEy: Standard Error of y Estimate against the Model Regression
Avg(y): Average of all y Data If the above expression exceeds the relative deviation limit a data set is characterized as invalid.

An additional application of the model is the detection and removal or correction of outliers. There are two straightforward implementations. One is to check each residual data deviation from the model regression against a pre-set limit and remove the outlier when exceeding that limit. It is possible to replace the detected outlier by the curve found by the regression model. A second implementation uses the relative total deviation of the whole curve from the model regression. If the criterion $$\frac{SEy}{Avg(y)} < \text{Relative Deviation Outlier Limit}$$

is passed there is no outlier removal. If it is failed the data point with the highest residual deviation is removed and the regression is made again. It is meaningful to have the pre-set criterion relative deviation outlier limit smaller than the relative deviation limit.

In the above formula, parameter $p_3$ has a particular importance. If in the growth curve $p_3$ is 0, then no signal growth has occurred. This translates to that the nucleic acid to be detected in the sample is not present. In the alternative, if $p_3$ is a positive value, the nucleic acid to be detected is present in the sample.

In order to determine a statistically significant growth, a criterion for the t-parameter for the null-hypothesis of the growth parameter $p_3$ is set according to the following t-test:

$$t_0(p_3=0) \text{ compared to } t=p_3*/c_{33}$$

$t_0$: pre-set discrimination limit for the t-value
t: t value for the null hypothesis ("negative")
$p_3*$: estimate of the growth model parameter
$c_{33}$: $3^{rd}$ diagonal element of the covariance matrix of the regression. This value estimates the standard error of the determined optimal parameter. It can be calculated from the inverse of the derivative matrix according to standard methods.

If the t value is smaller than a pre-set value it can be assumed that $p_3$ is not significantly different from zero (null hypothesis). The presence of a positive $p_3$ value in itself may be used as an indication for the presence of the analyte and the determination of a $p_3$ value to be 0 may be used as an indication of the absence of the particular analyte. This is useful when a qualitative determination is required. An appropriate message may be created in a data comparison unit in the analytical instrument or on a computer used for evaluation of the data and may be communicated to the user. In the alternative, the data may be stored in a memory and be connected with data from others sources and transferred elsewhere.

Figure 3:
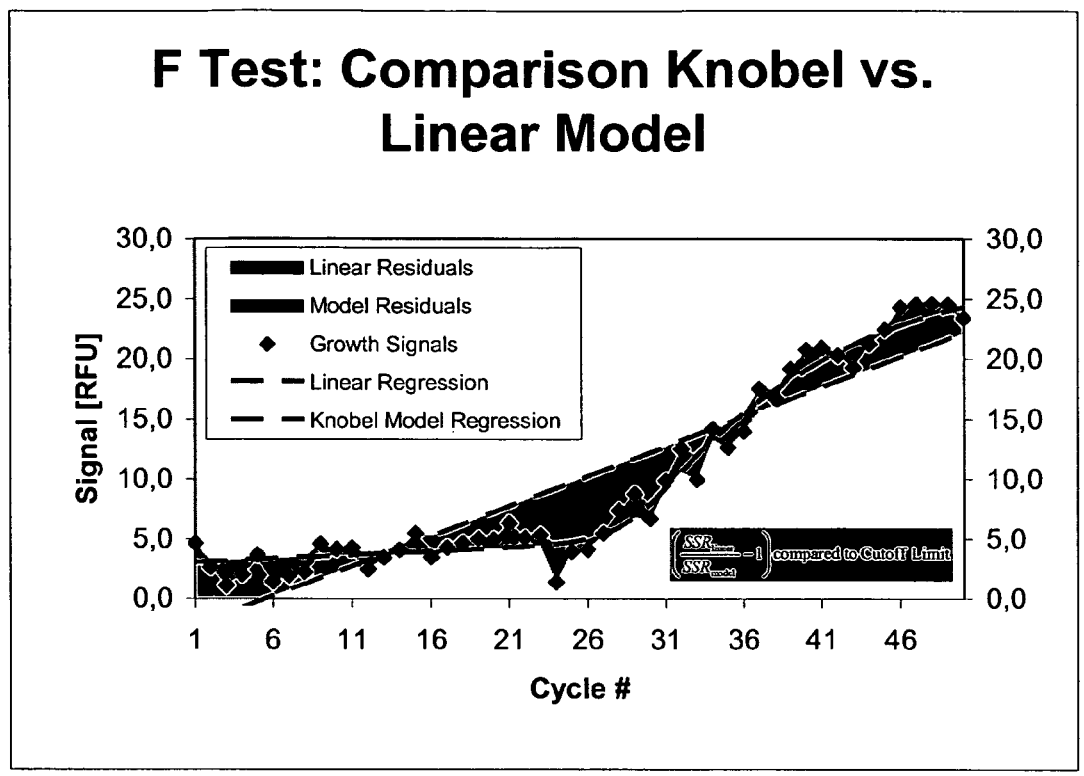
In FIG. 3 there is depicted a graphical representation of the F test of the method of the invention vs. a linear model.

Another method for qualitative determination of the presence of an analyte can be applied which is preferred for growth curves not reaching their saturation phase fully. This can happen with a small number of measurements or a late signal increase. The method consists of a statistical comparison of the negative curve (linear) estimation hypothesis and the full growth curve (model) estimation hypothesis. For this the sum of the square deviations from both the model regression and the linear regression is determined. Together with the appropriate numbers for the degrees of freedom a statistical F-test is performed. If the F value is smaller than a pre-set value it can be assumed that the full model curve is not significantly different from the linear regression (null hypothesis). FIG. 3 shows the graphical representation of that method. The mathematical representation of this test is shown in the following formula $$F = \left(\frac{SSR(L)}{SSR(M)} - 1\right) \cdot \frac{n-m}{m-2}$$

wherein there are

| | |
|---|---|
| F | calculated F-value |
| SSR(L) | Sum of squares of the residuals of a linear regression, |
| SSR(M) | Sum of squares of the residuals of the model regression, |
| n | Number of measurement data points, and |
| m | Number of model parameter, 7 in the model of formula I. |

$$SSR(L) = \sum_{i=1}^{n} y_i^2 - \frac{1}{n} \cdot \left(\sum_{i=1}^{n} y_i\right)^2 - \frac{\left(\sum_{i=1}^{n} (x_i \cdot y_i) - \frac{1}{n} \cdot \sum_{i=1}^{n} x_i \cdot \sum_{i=1}^{n} y_i\right)^2}{\sum_{i=r}^{n} x_i^2 - \frac{1}{n} \cdot \left(\sum_{i=1}^{n} x_i\right)^2}$$

$$SSR(M) = \sum_{i=1}^{n} \left(y_i - \hat{y}(x, \vec{p})\right)^2$$

wherein there are

| | |
|---|---|
| xi | cycle number of measurement data, |
| yi | measurement data, |
| $\hat{y}$ | calculated model value, and |
| p | model parameter. |

In detail, if the F value is smaller than a pre-set value (e.g. 20) it can be assumed that the present growth curve is not significantly different from a negative curve. The presence of an F value above a pre-set value in itself may be used as an indication of the presence of the analyte and the determination of an F value below a pre-set value may be used as an indication of the absence of the particular analyte. This is useful when a qualitative determination is required. An appropriate message may be created in a data comparison unit in the analytical instrument or on a computer used for evaluation of the data and may be communicated to the user. In the alternative, the data may be stored in a memory and be connected with data from others sources and transferred elsewhere.

A refinement of the regression process consists in simplifying the PCR model in case of one of the parameter $p_4$, $p_5$, $p_6$, $p_7$ being not significantly different from 0. For this a similar t-test for the parameter using the covariance matrix can be used. Then in a second step the refined PCR model can be used with $p_4'=p_5'=0$ and $p_3'=2*p_3$. This represents a simple sigmoid function with baseline drift and optional step. Then after a similar non-linear regression as described above the t-test for $p_3'$ can be made similarly for positive negative discrimination.

The result of the transformation of the measurement data to a growth curve using non-linear regression fitting of the growth curve using a model according to the invention leads to a final growth curve which is defined by optimized parameters. This growth curve relates each value on the X axis to a value on the Y axis that may be altered compared to the measurement data. Therefore, the growth curve conveniently corrects spike measurement data misread by the detector or created through false irradiation.

The next preferred step of the method according to the invention comprises comparing one or more growth curve characteristics to reference value(s). The reference values may differ dependent from the purpose of the determination. Typically, reference values consist of any one or the combination of the parameters of the growth curve of a reference measurement.

Figure 4:
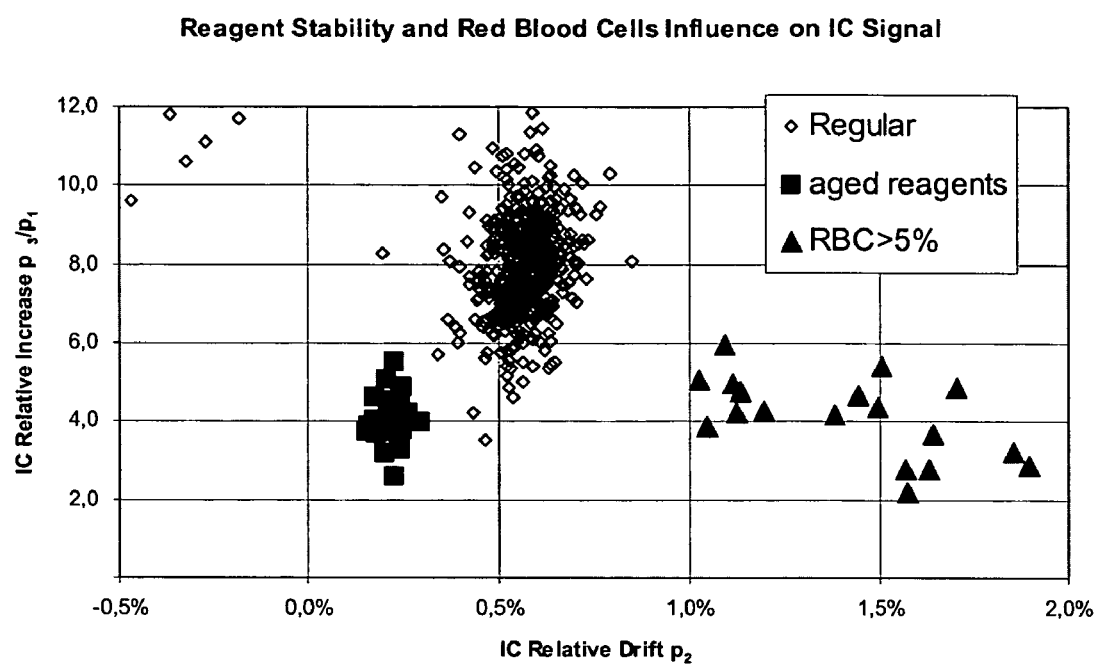
In FIG. 4 there is depicted the use of both p2 and p3/p1 as typical values of the parameters of the internal control signal as a measure for reagent expiry and/or increased red blood cell content in the sample.

Two examples are shown in FIG. 4. As typical values both p2 and p3/p1 are used. If the parameter values of the internal control signal are in the lower left range of the graph shown in FIG. 4, reagent expiry can be assumed. If the parameter values of the internal control signal are in the lower right portion of the graph, increased red blood cell content in the sample can be detected.

The present invention is useful for the qualitative determination of the analyte, i.e. the determination that the analyte is present in an amount exceeding a predefined threshold ("positive" or "negative"). In this case, it is preferred to use a statistical measure for determining the presence or absence of the analyte.

The present invention is also useful for quantitative determination of analytes, i.e. for determining the amount of analyte or its concentration in the sample. In this case, the optimized growth curve instead of the original measurement data is used. So, the negative effects of measurement data imprecision, e.g., measurement data outliers, are minimized. The further calculation steps for determining the final result can remain the same as in the standard method.

Another subject of the invention is an analytical instrument for determining the presence of an analyte comprising
a signal detection unit,
a signal to measurement data transformation unit,
a measurement data storage,
a measurement data to growth curve transformation unit,
a growth curve to digital data transformation unit, and
a growth curve comparison unit,
wherein said measurement data to growth curve transformation unit comprises a computer loaded with an algorithm for non-linear regression fitting of a growth curve to the measurement data using a growth curve model defined by between 5 and 11 parameters.

Such instruments can be assembled from commercially available units. The present invention, however, provides that less expensive units can be used to achieve the same or even superior results in the determination of analytes. Particularly, the signal detection unit used in the instrument of the present invention can be chosen to be less precise. This is the case for e.g. an analog to digital converter with reduced number of digits, omission of pre-amplifiers or a darker light source. An especially attractive option is to user narrower wavelength transmission filters which results in a reduction of light crossover (crosstalk or bleed-over) in case of a parallel multicolor detection of multiple analytes. The units according to the invention do not need to be physically separated, but can be combined in one or more combined units.

In one aspect of the invention, the instrument comprises a light source. Again, as the algorithm of the present invention can sort out much better spikes created by varying intensities of the light source, much cheaper light sources can be used than presently, or less stabilization of the light source is needed.

In another aspect of the invention, the signal is a fluorescent signal. The light detectors are adapted to be capable of receiving and detecting the fluorescent light.

One model used in the computer program running on the instrument is based on the formula $$f(x) = p_1 \cdot (1 + p_2 \cdot x) + \frac{p_3}{[1 + \exp\{-p_4 \cdot (x - p_5)\}] \cdot [1 + \exp\{-p_6 \cdot (x - p_7)\}]}$$

or its mathematic equivalents.

The instrument can be used for quantitative determination of the analyte, if said computer is further loaded with an algorithm to select a value on said growth curve indicative of the concentration of said nucleic acid present in said sample.

Advantages of using the new algorithm are manifold. Due to imprecision of assays produced by e.g., unexpected events during the measurement, like spikes, measurement data can be incorrect. The new algorithm improves the correction of such wrong data. On the other side, components of instruments used for the detection can contribute to variations in measurement data not related to the presence of the analyte, for example by variation of the intensity of light provided by the light source. Such variants can also be corrected by the new growth curve model. Furthermore, it is possible to use components in the instrument which have reduced precision, because the model will correct the imprecision created by this component.

The method of the invention for the comparison of the growth curves uses accurately determined characteristic numbers of the growth curve and statistically estimates any error, e.g. in $C_T$, Baseline intercept, baseline drift (slope), maximal signal level (relating to 100% oligonucleotide probe cleavage, hybridization, intercalation or the like), cleavage efficiency, amplification efficiency, relative and absolute signal increase, threshold cycle numbers first or second derivative maximum and other "elbow" measures.

An exemplary growth curve showing the physical meaning of the parameters according to the invention is shown in FIG. 1. It shows the measurement data in light dots, a continuous growth curve, a base line (lower line) and a saturation line (upper line). $p_1$ is the y-value for x=0 on the base line, $p_2$ is the slope of the base line, $p_3$ is the y-value for x=0 on the saturation line, $p_4$ is the slope of the growth curve at x value of $p_5$, and $p_6$ is the slope of the growth curve at $x=p_7$.

A further subject of the invention is a computer program for determining the presence of an analyte from measurement data comprising
creating a growth curve from measurement data through a mathematical algorithm, wherein said mathematical algorithm comprises a growth curve model formula defined by between 5 and 11 parameters which are determined by non-linear regression fitting.

The details of the computer program are described above for the method and the instrument of the invention. Particularly, the computer program may be preferably loaded on the instrument according to the invention in order to direct the steps of the method of the invention on the instrument including its units according to the invention. In another embodiment the computer program may also be recorded on a computer-readable medium.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for determining the presence of a nucleic acid in a sample, comprising:
providing a reaction mixture suspected of containing a nucleic acid, wherein said reaction mixture is in a form suitable for eliciting a detectable signal from said suspected nucleic acid,
detecting said signals from said reaction mixture in known intervals,
transforming said signals into measurement data, and
creating from said measurement data a growth curve through a mathematical algorithm,
wherein said mathematical algorithm comprises a mathematical growth curve model formula $$f(x) = p_1 \cdot (1 + p_2 \cdot x) + \frac{p_3}{[1 + \exp\{-p_4 \cdot (x - p_5)\}] \cdot [1 + \exp\{-p_6 \cdot (x - p_7)\}]}$$

or its mathematic equivalents, wherein

| | |
|---|---|
| x | is a measure of the time or sequence of the measurements, |
| $p_1$ | is the intercept of the growth curve for the start of the reaction, |
| $p_2$ | is the relative drift of the base line, |
| $p_3$ | is the distance between the base line and the saturation line, |
| $p_4$ | is the slope at the inflection point of a first multiplicative sigmoid function representing exponential growth, |
| $p_5$ | is the inflection point of a first multiplicative sigmoid function, |
| $p_6$ | is the slope at the inflection point of a second multiplicative sigmoid function representing saturation growth, and |
| $p_7$ | is the inflection point of a second multiplicative sigmoid function, wherein optimal values of the parameters are determined by a non-linear aggression fitting algorithm to said measurement data, | determining from said growth curve whether said nucleic acid is present or absent in said reaction mixture.

2. The method according to claim 1, wherein said parameters of the said growth curve model formula are determined using a non-linear regression fitting algorithm, wherein
the starting values for said parameters are generated using said measurement data,
the range of said parameters are checked, and
automatic algorithm stopping criteria are employed.

3. The method according to claim 1, wherein for further calculations said measurement data are partially or fully replaced by data generated using said growth curve model.

4. The method according to claim 1, further comprising comparing one or more data characteristic for said growth curve to corresponding reference values.

5. The method according to claim 1, further comprising determining a value from said growth curve indicative of the concentration of said nucleic acid present in said sample.

6. The method according to claim 1, wherein a statistical test is used for comparison with said background curve estimation.

7. The method according to claim 1, wherein the quality of components leading to the final result is determined.

8. A method for determining the presence of a nucleic acid in a sample, comprising:
providing a reaction mixture suspected of containing a nucleic acid, wherein said reaction mixture is in a form suitable for eliciting a detectable signal from said suspected nucleic acid,
detecting said signals from said reaction mixture in known intervals,
transforming said signals into measurement data, and
creating from said measurement data a growth curve through a mathematical algorithm,
wherein said mathematical algorithm comprises a mathematical growth curve model formula $$f(x) = p_1 \cdot (1 + p_2 \cdot x) + \frac{p_3}{[1 + \exp\{-p_4 \cdot (x - p_5)\}] \cdot [1 + \exp\{-p_6 \cdot (x - p_7)\}]} - \frac{p_8}{2}[1 + \text{sign}\{s - x + 0.5\}]$$

or its mathematic equivalents wherein

| | |
|---|---|
| $p_1$ | is the intercept of the growth curve for the start of the reaction, |
| $p_2$ | is the relative drift of the base line, |
| $p_3$ | is the distance between the base line and the saturation line, |
| $p_4$ | is the slope at the inflection point of a first multiplicative sigmoid function representing exponential growth, |
| $p_5$ | is the inflection point of a first multiplicative sigmoid function, |
| $p_6$ | is the slope at the inflection point of a second multiplicative sigmoid function representing saturation growth, |
| $p_7$ | is the inflection point of a second multiplicative sigmoid function, wherein optimal values of the parameters are determined by a non-linear aggression fitting algorithm to said measurement data, |
| $p_8$ | is the signal step size at a point where measurement conditions change, and sign means the function sign $(x) := x/\sqrt{(x^2)}$, $x \neq 0$; sign $(0) := 0$ and s a pre-set step cycle number from which on a measurement condition has changed, | determining from said growth curve whether said nucleic acid is present or absent in said reaction mixture.

* * * * *